(12) United States Patent
Taneja

(10) Patent No.: US 9,849,091 B1
(45) Date of Patent: Dec. 26, 2017

(54) SOLID ORAL FORMULATIONS HAVING AN IRON SUGAR OVERCOAT

(71) Applicant: Jugal K. Taneja, Tampa, FL (US)

(72) Inventor: Jugal K. Taneja, Tampa, FL (US)

( * ) Notice: Subject to any disclaimer, the term of this patent is extended or adjusted under 35 U.S.C. 154(b) by 0 days.

(21) Appl. No.: 14/753,776

(22) Filed: Jun. 29, 2015

(51) Int. Cl.
*A61K 9/28* (2006.01)
*A61K 47/26* (2006.01)
*A61K 47/02* (2006.01)

(52) U.S. Cl.
CPC .......... *A61K 9/2813* (2013.01); *A61K 9/2826* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,521,247 B1 * | 2/2003 | deVries | A23L 33/16 424/439 |
| 6,994,872 B2 * | 2/2006 | Takeuchi | A61K 9/2826 424/400 |
| 2006/0251722 A1 * | 11/2006 | Bandak | A61K 9/2081 424/472 |

* cited by examiner

*Primary Examiner* — Brian J Davis

(57) ABSTRACT

This invention provides a solid oral formulation including a tablet core surrounded by an iron sugar overcoat so that the iron sugar overcoat makes at least some elemental iron content available for gastrointestinal absorption relative to the tablet core while counteracting at least some of the constipation associated with oral iron consumption, and further includes methods of administering the solid oral formulation.

22 Claims, No Drawings

SOLID ORAL FORMULATIONS HAVING AN IRON SUGAR OVERCOAT

The present invention provides a solid oral formulation including a tablet core surrounded by an iron sugar overcoat so that the iron sugar overcoat makes at least some elemental iron content available for gastrointestinal absorption relative to the tablet core while counteracting at least some of the constipation associated with oral iron consumption. The term "iron" herein may refer to an elemental iron equivalent content that is available for absorption, unless otherwise stated, or may refer to a specific source of iron, e.g., ferrous sulfate.

BACKGROUND OF THE INVENTION

Iron is an essential mineral, trace element involved in electron transport and numerous enzymatic redox reactions that take place in the body, such as oxidative phosphorylation that provides the body with energy. Iron also forms the essential heme prosthetic group of hemoglobin, that makes oxygen transport by red blood cells possible, and of myoglobin, that allows muscle cells to store oxygen for utilization. Without sufficient iron, mammalian life is just not possible. Iron present in the body beyond what is immediately needed for functional purposes is stored. Too much iron can cause iron overload that results in iron-mediated oxidative stress damage to cells and organs. Too little iron can cause an iron deficiency, and if prolonged, results in iron deficiency anemia as ferritin cellular iron stores are depleted followed by transferrin transport iron. This depleted state reduces red blood cell production and leads to unhealthy, small and pale, red blood cells. For these reasons, iron homeostasis is generally well regulated in the body, and in healthy individuals, iron recycling is very efficient. However, unhealthy individuals and different circumstances and illnesses can lead to much greater iron loss. Conditions that can lead to iron deficiency include malnutrition, iron absorption or retention disorders, irritable bowel syndrome, as well as, pregnancy, blood loss, such as from menses, medication induced intestinal bleeding, such as from aspirin and other nonsteroidal anti-inflammatory drugs, NSAIDs, gastric ulcers, and parasitic gastrointestinal infections.

Regulation of iron balance occurs mainly in the gastrointestinal tract through absorption. This absorptive process is both regulated and inefficient, to prevent the excess intake of iron. When diet alone cannot maintain or restore deficient iron levels, iron supplementation is often necessary. Oral iron preparations have been used medicinally for many centuries. It has been fabled that oral iron has been used in antiquity, as early as 4000 B.C., to treat hemorrhagic losses in wounded Persian soldiers. In the modern era of medicine, French physician P. Blaud de Beaucaire is credited with administration of iron pills to treat anemia circa 1831. Advertisements for the sale of pharmaceutical preparations of ferrous iron appeared in United States medical journals as early as 1850. The medicinal uses of iron as a treatment for iron deficiency anemia, and how oral iron administration induces increased red blood cell formation in these patients as a hematinic agent, have been detailed in encyclopedias since 1900, and proven in clinical studies over the last century.

There are various forms of iron that have been provided as oral supplements. These include both the ferrous iron and ferric iron forms, most often as iron salts, e.g., ferric sulfate, ferrous sulfate, ferrous fumarate, ferrous gluconate, and sodium ferric gluconate. Further oral iron examples include iron amino chelate, iron polymaltose complex, carbonyl iron, and heme derived iron. These various forms of iron have different compound weights. Furthermore, various forms of iron can be anhydrous, or exist in one or more different hydration states, each having their own weight. For example, ferrous sulfate has five different hydration states in addition to the anhydrous form. Therefore, when referring to various iron formulations, it is often necessary to standardize the iron content in the form of an elemental iron equivalent content. For instance, 200 mg of ferrous sulfate, depending on its hydration state, often contains approximately 65 mg of elemental iron equivalent.

The prior art shows various multivitamin tablet configurations, including iron tablets having an enteric coating, tablets composed of a slow and fast release formulation of iron, and tablets with an iron core. However, none of the prior art describes or teaches a solid oral formulation including a tablet core surrounded by an iron sugar overcoat so that the iron sugar overcoat makes at least some elemental iron content available for gastrointestinal absorption relative to the tablet core while counteracting at least some of the constipation associated with oral iron consumption. The tablet core includes at least one therapeutic ingredient. This tablet core is surrounded by an iron sugar overcoat. The iron sugar overcoat includes at least one form of bioavailable iron and at least one sugar. This iron sugar overcoat makes available at least some elemental iron content for gastrointestinal absorption either prior to the release of the at least one therapeutic ingredient of the tablet core, or concomitant to the release and absorption of the at least one therapeutic ingredient of the tablet core. In this sense, the relative release and absorption of iron from the iron sugar overcoat is controlled relative to the release and absorption of the at least one therapeutic ingredient of the tablet core. Iron transporters of the intestines can be primed with iron prior to the absorption of the at least one therapeutic ingredient of the tablet core. The iron sugar overcoat, and any iron contained in the core, can help reduce gastrointestinal bleeding, help maintain iron levels in the body, or help replenish iron levels in the body. Therefore, the solid oral formulation can therefore help prevent or treat iron deficiency or iron deficiency anemia. In one embodiment of the invention, the sugar overcoat provides at least some iron to counteract the iron loss due to gastrointestinal bleeding caused by NSAIDs, and as a styptic, antihemorrhagic agent, e.g., ferric sulfate or ferrous sulfate, reduce gastrointestinal bleeding. As such, this embodiment may contain an NSAID core. In another embodiment of the invention, the sugar overcoat provides at least some iron to counteract the iron loss associated with irritable bowel syndrome, IBS, and can help treat its symptoms. As such, this embodiment may contain an IBS drug core, e.g., dicyclomine, an anticholinergic. Importantly, the at least one sugar of said iron sugar overcoat is what has some laxative effect that counteracts at least some of the constipation associated with oral iron consumption. Many other beneficial therapeutic ingredients can be envisioned for the solid oral formulations according to this invention.

DESCRIPTION OF THE INVENTION

The present invention relates to solid oral formulations having an iron sugar overcoat, an iron-containing sugar coating, or a sugar coating of pharmaceutically acceptable salts or chelates of iron, which are useful in oral administrations for iron supplementation and raising blood iron stores, such as for treating iron deficiency and iron deficiency anemia, as well as, having a synergistic or antagonistic effect in combination with other pharmaceutically active ingredients, such as for reducing iron loss from gastrointestinal bleeding and reducing gastrointestinal bleeding. Iron has been shown to possess hematinic activity and styptic activity. Because iron may impact gastrointestinal motility or cause constipation, the at least one sugar of said iron sugar overcoat has some laxative effect that helps counter at least some of the constipation associated with oral iron consumption.

This invention provides a solid oral formulation including a tablet core and an iron sugar overcoat. The tablet core includes at least one therapeutic ingredient. This tablet core is surrounded by the iron sugar overcoat. The iron sugar overcoat includes at least one form of bioavailable iron and at least one sugar. The iron sugar overcoat can make available at least some elemental iron content for gastrointestinal co-absorption with the at least one therapeutic ingredient of said tablet core. Alternatively, the iron sugar overcoat can make available at least some elemental iron content for gastrointestinal absorption prior to the release of said at least one therapeutic ingredient of said tablet core, so as to prime iron transporters in the intestines prior to absorption of the at least one therapeutic ingredient of said tablet core. The at least one sugar of said iron sugar overcoat further has some laxative effect that counteracts at least some of the constipation associated with oral iron consumption.

The tablet core includes at least one therapeutic ingredient, and in some embodiments, is structured as a pellet/granule. It is contemplated that when the formulations of this invention are used, they can be administered in conjunction with one or more other pharmaceutically active ingredients comprising the tablet core. The at least one therapeutic ingredient of the tablet core is selected from the group of inorganic and organic compounds including vitamins, minerals, proteins, carbohydrates, and lipids. In a first preferred embodiment, the at least one therapeutic ingredient of the tablet core is a bioavailable form of iron selected from the group of iron-containing compounds and molecules including compounds and molecules containing ferrous iron, compounds and molecules containing ferric iron, iron salts, ferric sulfate, ferrous sulfate, ferrous fumarate, ferrous gluconate, sodium ferric gluconate, iron amino chelate, iron polymaltose complex, carbonyl iron, and heme derived iron. As such, the bioavailable form of iron of the tablet core further has or causes at least one physical effect selected from the group including reducing gastrointestinal bleeding, maintaining iron levels in the body, replenishing iron levels in the body, raising iron levels in the body, preventing iron deficiency anemia, preventing iron deficiency, treating iron deficiency, and treating iron deficiency anemia. It is believed that by priming the intestinal iron transporters with a small dose of iron, it can then make for more efficient absorption and transport of a larger iron dose that immediately follows, including iron released from the tablet core. Intestinal iron transporters can include divalent metal transporter 1 and ferroportin. Priming divalent metal transporter 1 with iron, may also affect absorption of other divalent metals such as cadmium, copper, manganese, and zinc. Enzymes, including ferric reductase, can also be primed or saturated with iron to influence their kinetics or expression levels, which can influence the uptake of subsequent iron.

In most embodiments, the at least one therapeutic ingredient of the tablet core is an active pharmaceutical ingredient. In a second preferred embodiment, the at least one therapeutic ingredient of the tablet core is a nonsteroidal anti-inflammatory drug. The at least one therapeutic ingredient is selected from the group of NSAIDs including: Aspirin (acetylsalicylic acid), Diflunisal (Dolobid), Salicylic acid and other salicylates, Salsalate (Disalcid); Ibuprofen, Dexibuprofen, Naproxen, Fenoprofen, Ketoprofen, Dexketoprofen, Flurbiprofen, Oxaprozin, Loxoprofen; Indomethacin, Tolmetin, Sulindac, Etodolac, Ketorolac, Diclofenac, Aceclofenac, Nabumetone; Piroxicam, Meloxicam, Tenoxicam, Droxicam, Lornoxicam, Isoxicam, Phenylbutazone; Mefenamic acid, Meclofenamic acid, Flufenamic acid, Tolfenamic acid; Celecoxib, Rofecoxib, Valdecoxib, Parecoxib, Lumiracoxib, Etoricoxib, Firocoxib; and Nimesulide. These examples of NSAIDs are not meant to be exhaustive. And while most embodiments for this invention apply to human patients, the solid oral formulation can be applied to veterinary patients, of which, some NSAIDs may be more appropriate for animals. NSAIDs are associated with causing gastrointestinal bleeding, of which, can cause iron loss. The bioavailable iron in the iron sugar overcoat, and in some instances, of the tablet core, can replenish this iron loss as hematinic agent and help stop the bleeding as a styptic agent. The present invention affords great advantages over prior NSAID formulations.

In a third preferred embodiment, the at least one therapeutic ingredient of the tablet core is an irritable bowel syndrome drug selected from the group including anticholinergics. In one example, the at least one therapeutic ingredient is dicyclomine. Irritable bowel syndrome (IBS) is often associated with iron deficiency or iron deficiency anemia due to poor iron absorption. Supplemental iron can help. The present invention can help treat the iron deficiency associated with IBS while in the same drug formulation used to treat symptoms of IBS, such as hypermotility.

The present invention can include various combinations of therapeutic and active pharmaceutical ingredients in its tablet core. The above examples are not meant to be limiting. The therapeutic ingredient of the tablet core may be released immediately or by a controlled-release formulation. The tablet core will often further include at least one excipient. The at least one excipient of the tablet core is selected from the group of excipients including fillers, binders, solvents, coating excipients, and release-modifying excipients.

In all embodiments, the tablet core is surrounded by the iron sugar overcoat. The iron sugar overcoat includes at least one form of bioavailable iron and at least one sugar. The at least one form of bioavailable iron of the iron sugar overcoat is selected from the group of iron-containing compounds and molecules including compounds and molecules containing ferrous iron, compounds and molecules containing ferric iron, iron salts, ferric sulfate, ferrous sulfate, ferrous fumarate, ferrous gluconate, sodium ferric gluconate, iron amino chelate, iron polymaltose complex, carbonyl iron, and heme derived iron. The at least one form of bioavailable iron of said iron sugar overcoat further has or causes at least one physical effect selected from the group including reducing gastrointestinal bleeding, maintaining iron levels in the body, replenishing iron levels in the body, raising iron levels in the body, preventing iron deficiency anemia, preventing iron deficiency, treating iron deficiency, and treating iron deficiency anemia. The iron sugar overcoat can make available at least some elemental iron content for gastrointestinal co-absorption with the at least one therapeutic ingredient of said tablet core. Alternatively, the iron sugar overcoat can make available at least some elemental iron content for gastrointestinal absorption prior to the release of said at least one therapeutic ingredient of said tablet core, so as to prime iron transporters in the intestines prior to absorption of the at least one therapeutic ingredient of said tablet core.

The iron sugar overcoat preferably has some sweet taste to mask the taste of the at least one form of bioavailable iron in the iron sugar overcoat. The sweet taste can improve patient compliance and make swallowing easier. However, the sugar in the iron sugar overcoat can serve an even more important function. The at least one sugar of said iron sugar overcoat further has some laxative effect that counteracts at least some of the constipation associated with oral iron consumption. The at least one sugar of the iron sugar overcoat is selected from the class of sugars behaving as soluble fiber or the class of sugar alcohols. In preferred embodiments, the at least one sugar of the iron sugar overcoat is selected from the class of less digestible/hard-to-digest sugars including polydextrose, oligofructose, maltitol, xylitol, sorbitol, lactulose, and mannitol. Sugar alcohols are not fully broken down during digestion. Other sugars, such as lactulose, are not digestible. However, they share a similar osmotic effect, causing the retention of water through osmosis in the large intestine or colon, which serves as a stool softener and stimulates bowel movements. Some of these sugars, including lactulose, can also lower pH due to their fermentation by gut flora to have another laxative effect. The effects on aiding bowel movement will counteract some of the constipation caused by oral iron, thereby, fulfilling a medically important need in reducing a major side effect associated with oral iron.

If desired, additional sugar sweeteners can also be including or substituted in one or more coating layers or even the iron sugar overcoat. Additional sugar sweeteners can include sucrose, derived from beet or cane sources or starch, saccharide, or polysaccharide converted sources, or artificial sweeteners including sucralose, aspartame, or saccharin.

The iron sugar overcoat in most embodiments will further include at least one excipient. The at least one excipient of the iron sugar overcoat is selected from surface modifying agents, solvents, and binders. When surface modifying agents are used in preparing the iron sugar overcoat, these can include various polymers, low molecular weight oligomers, natural products and surface modifying agents. Preferred surface modifying agents include nonionic and anionic surface modifying agents. Representative examples of surface modifying agents include, but are not limited to, poloxamer 188, calcium benzalkonium chloride, stearate, cetostearl alcohol, cetomacrogol emulsifying wax, sorbitan esters, colloidol silicon dioxide, phosphates, sodium dodecylsulfate, magnesium aluminum silicate, and triethanolamine. When binders are used in preparing the iron sugar overcoat, these can include gum acacia, tragacanth, stearic acid, gelatin, casein, lecithin (phosphatides), carboxymethylcellulose calcium, carboxymethylcellulose sodium, methylcellulose, hydroxyethylcellulose, hydroxypropylcellulose, hydroxypropylmethycellulose phthalate, methyacrylate, microcrystalline cellulose, noncrystalline cellulose, polyvinylpyrrolidone (povidone, PVP), cetostearyl alcohol, cetyl alcohol, cetyl esters wax, dextrates, dextrin, lactose, dextrose, glyceryl monooleate, glyceryl monostearate, glyceryl palmitostearate, polyoxyethylene alkyl ethers, polyethylene glycols, polyoxyethylene castor oil derivatives, polyoxyethylene stearates, polyvinyl alcohol, and sorbitan fatty acid esters. These examples are not meant to be exhaustive nor limiting.

The iron sugar overcoat, in other embodiments, can further include at least one additional ingredient, an at least one pharmaceutically active ingredient other than a form of bioavailable iron and sugar laxative. This at least one pharmaceutically active ingredient other than a form of bioavailable iron and sugar laxative can be in some way complementary or synergistic to the therapeutic ingredient of the tablet core. For example, the pharmaceutically active ingredient can be an additional laxative, such as a sennoside. Or, the pharmaceutically active ingredient of the iron sugar overcoat could be an antidepressant, such as desipramine, which can help with the pain associated with IBS, while the dicyclomine antispasmodic of the tablet core helps with hypermotility.

Attention is now drawn to some of the preferred formulations and methods of manufacturing tablets according to the present invention.

In the following examples, the tablet core is prepared by the method of direct compression or the method of dry granulation. In other embodiments, the process starts with a pre-made pellet containing active ingredient. The tablet core is surrounded by an iron sugar overcoat. The formulation for the tablet cores and the tablet coating layers are provided separately. The acronyms USP stands for United States Pharmacopeia, while the acronym NF stands for National Formulary.

EXAMPLE 1 is of the first preferred embodiment of iron tablets. This tablet is a ferrous sulfate tablet, USP 200 mg tablet, which contains 193.846 mg of ferrous sulfate in its tablet core and 6.154 mg of ferrous sulfate in its iron sugar overcoat, for a total elemental iron content of about 65 mg.

The tablet core weighs 340 mg, while the coated tablet weighs 435 mg.

The tablet core includes:
Dried Ferrous Sulfate, USP, 193.846 mg; Microcrystalline Cellulose, NF (Avicel PH-102), 84.274 mg; Copovidone, USP (Kollidon VA 64), 17.000 mg; Pregelatinized Starch, NF (Starch 1500 LM Partially Pregelatinized Maize Starch), 22.500 mg; Croscarmellose Sodium, NF (Ac-Di-Sol SDW-802), 17.000 mg; Sodium Lauryl Sulfate, NF, 3.000 mg; and Magnesium Stearate, NF, 2.380 mg.

The tablet core is prepared by direct compression. Briefly, the first six ingredients are sifted by using a suitable sifter and are blended in a suitable blender for a sufficient period of time. Then sifted Magnesium Stearate is added and the blending is continued for a suitable period of time and the final lubricated blend is compressed into tablets by using a suitable compression machine.

The iron sugar overcoat includes:
Dried Ferrous Sulfate, USP, 6.154 mg; Polydextrose, 83.946 mg; Povidone, 3.200 mg; Microcrystalline Cellulose, NF (Avicel PH-102), 1.700 mg; and Water, 57.750 mg. Most or all of the water content is removed as the overcoat is dried.

The compressed tablets are subjected to iron sugar overcoating by using the iron sugar coating suspension and suitable coating machine. The final iron sugar overcoated tablets are packed into a suitable container.

In this example, the Polydextrose serves as the less digestible/hard-to-digest sugar that behaves as soluble fiber and has some laxative effect that counteracts at least some of the constipation associated with oral iron consumption. This example provides an iron sugar overcoated iron tablet for maintaining iron levels in the body, replenishing iron levels in the body, raising iron levels in the body, preventing iron deficiency anemia, preventing iron deficiency, treating iron deficiency, and treating iron deficiency anemia. It was found desirable for the formulation to be optimized so that iron transporters of the intestines are primed with iron from the iron sugar overcoat prior to the bulk of the absorption of the iron derived from the tablet core. This tablet should be taken 2-3 times per day for several months to treat iron deficiency anemia by providing a daily elemental iron equivalent of 130 to 195 mg; and taken at least once per day for several additional months to replenish iron stores in the body by providing a daily elemental iron equivalent of 65 mg.

EXAMPLE 2 is of a second preferred embodiment of NSAID tablets, an ibuprofen tablet, containing an iron sugar overcoat. This tablet contains ibuprofen 200 mg in the tablet core and 6.154 mg of ferrous sulfate (equivalent to approximately 2 mg of elemental iron) in its iron sugar overcoat.

The tablet core weighs 400 mg, while the coated tablet weighs 495 mg.

The tablet core includes:
Ibuprofen, 200.000 mg; Lactose, 144.800 mg; Methyl Cellulose, 14.500 mg; Pregelatinized Starch, NF (Starch 1500 LM Partially Pregelatinized Maize Starch), 18.500 mg; Sodium Starch Glycolate, 15.000 mg; Colloidal Silicon Dioxide, 3.200 mg; and Magnesium Stearate, NF 4.000 mg.

The tablet core is prepared by dry granulation. The first six ingredients, while leaving some Lactose and Sodium Starch Glycolate remaining, are sifted using a suitable sifter and blended using a suitable blender for a sufficient period of time and this premix blend is loaded into a compactor for formation of ribbons, i.e., dry granulation. These dried ribbons are milled by using a suitable mesh and co-mill. The milled granules are sifted through a suitable mesh along with the remaining quantity of Lactose and Sodium Starch Glycolate, and are blended for a suitable period of time. The Magnesium Stearate is then added to the blend and blending continues for a suitable period of time. The final lubricated blend is compressed into tablets by using a suitable compression machine.

The iron sugar overcoat includes:
Dried Ferrous Sulfate, USP, 6.154 mg; Sorbitol, 83.946 mg; Povidone, 3.200 mg; Microcrystalline Cellulose, NF (Avicel PH-102), 1.700 mg; and Water, 57.750 mg. Most or all of the water content is removed as the overcoat is dried.

The compressed tablets are subjected to iron sugar overcoating by using the iron sugar coating suspension and suitable coating machine. The final iron sugar overcoated tablets are packed into a suitable container.

In this example, the Sorbitol serves as the less digestible/hard-to-digest sugar that is a sugar alcohol and has some laxative effect that counteracts at least some of the constipation associated with oral iron consumption. This example provides an iron sugar overcoated ibuprofen tablet, with some bioavailable iron for reducing gastrointestinal bleeding associated with ibuprofen, and providing some replenishment of iron levels associated with such gastrointestinal bleeding. If this tablet is administered six times per day, such as for chronic pain, then this embodiment example can provide a daily elemental iron equivalent content of 12 mg, which can replenish iron levels over a multi-day or multi-week dosing regimen of this NSAID to prevent iron deficiency.

EXAMPLE 3 is of a second preferred embodiment of NSAID tablets, an aspirin tablet, containing an iron sugar overcoat. This tablet contains aspirin 100 mg in the tablet core and 24.615 mg of ferrous sulfate (equivalent to approximately 8 mg of elemental iron) in its iron sugar overcoat.

The tablet core weighs 235 mg, while the coated tablet weighs 340 mg.

The tablet core includes:
Aspirin, 100.000 mg; Lactose, 85.900 mg; Sucrose, 25.000 mg; Pregelatinized Starch, NF (Starch 1500 LM Partially Pregelatinized Maize Starch), 18.000 mg; Saccharin Sodium, 2.000 mg; Talc, 1.800 mg; and Magnesium Stearate, NF, 2.300 mg.

The tablet core is prepared by dry granulation. The first five ingredients, while leaving some Lactose and Pregelatinized Starch remaining, are sifted using a suitable sifter and blended using a suitable blender for a sufficient period of time and this premix blend is loaded into a compactor for formation of ribbons, i.e., dry granulation. These dried ribbons are milled by using a suitable mesh and co-mill. The milled granules are sifted through a suitable mesh along with the remaining quantity of Lactose and Pregelatinized Starch, and are blended for a suitable period of time. The Talc and Magnesium Stearate are then added to the blend and blending continues for a suitable period of time. The final lubricated blend is compressed into tablets by using a suitable compression machine.

The iron sugar overcoat includes:
Dried Ferrous Sulfate, USP, 24.615 mg; Lactulose, 55.100 mg; Maltitol, 21.585 mg; Povidone, 2.500 mg; Microcrystalline Cellulose, NF (Avicel PH-102), 1.200 mg; and Water, 54.000 mg. Most or all of the water content is removed as the overcoat is dried.

The compressed tablets are subjected to iron sugar overcoating by using the iron sugar coating suspension and suitable coating machine. The final iron sugar overcoated tablets are packed into a suitable container.

In this example, the Lactulose and Maltitol serve as less digestible/hard-to-digest sugars that have some laxative effect that counteracts at least some of the constipation associated with oral iron consumption. This example provides an iron sugar overcoated aspirin tablet, with considerable bioavailable iron for reducing gastrointestinal bleeding associated with aspirin, and able to provide a daily iron requirement (8 mg elemental iron equivalent) if the tablet is taken once per day as part of a daily aspirin regiment. If used for treating chronic pain, 2 to 6 tablets taken four times per day can simultaneously treat any iron deficiency or iron deficiency anemia associated with this NSAID use, with a daily intake of 64 to 192 mg of elemental iron equivalent.

EXAMPLE 4 is of a third preferred embodiment of IBS drug, anticholinergic tablets; a Dicyclomine HCl tablet containing an iron sugar overcoat. This tablet contains Dicyclomine HCl, USP 20 mg in the tablet core and 55.385 mg of ferrous sulfate (equivalent to approximately 18 mg of elemental iron) in its iron sugar overcoat.

The tablet core weighs 125 mg, while the coated tablet weighs 225 mg.

The tablet core includes:
Dicyclomine HCl, USP, 20.000 mg; Lactose, 65.100 mg; Microcrystalline Cellulose, NF (Avicel PH-102), 23.000 mg; Pregelatinized Starch, NF (Starch 1500 LM Partially Pregelatinized Maize Starch), 14.500 mg; Talc, 1.200 mg; and Magnesium Stearate, NF, 1.200 mg.

The tablet core is prepared by direct compression. Briefly, the first four ingredients are sifted by using a suitable sifter and are blended in a suitable blender for a sufficient period of time. Then sifted Talc and Magnesium Stearate are added and the blending is continued for a suitable period of time and the final lubricated blend is compressed into tablets by using a suitable compression machine.

The iron sugar overcoat includes:
Dried Ferrous Sulfate, USP, 55.385 mg; Oligofructose, 41.965 mg; Povidone, 2.000 mg; Microcrystalline Cellulose, NF (Avicel PH-102), 0.650 mg; and Water, 42.000 mg. Most or all of the water content is removed as the overcoat is dried.

The compressed tablets are subjected to iron sugar overcoating by using the iron sugar coating suspension and suitable coating machine. The final iron sugar overcoated tablets are packed into a suitable container.

In this example, the Oligofructose serves as the less digestible/hard-to-digest sugar that behaves as soluble fiber and has some laxative effect that counteracts at least some of the constipation associated with oral iron consumption. This example provides an iron sugar overcoated Dicyclomine HCl tablet for treating symptoms of IBS, while simultaneously treating the iron deficiency or iron deficiency anemia often associated with IBS. If administered four times per day for chronic use, this embodiment example can provide a daily elemental iron equivalent content of 72 mg, which can gradually treat iron deficiency anemia associated with IBS.

These above four examples are not meant to be limiting, and other formulations, excipients, and processes can be used or substituted in the examples above. Other bioavailable forms of iron can be substituted for, or added in combination with, the ferrous sulfate included in these examples, bioavailable forms of iron including other ferrous iron forms, compounds and molecules containing ferric iron, iron salts, ferrous fumarate, ferrous gluconate, sodium ferric gluconate, iron amino chelate, iron polymaltose complex, carbonyl iron, and heme derived iron. For instance, the first example can alternatively include a similar iron sugar overcoat of ferrous sulfate, but with a tablet core containing ferrous fumarate in an amount of about 64 mg elemental iron equivalent.

In the above four examples, solid oral formulations including a tablet core are surrounded by an iron sugar overcoat of approximately 100 mg. About 40 to 60 mg of water is used in preparing the about 100 mg iron sugar overcoat; the water is subsequently removed during processing. Briefly, iron is either milled using conventional milling techniques, for example with a Fitz or ball mill, or is micronized using conventional micronizing techniques, for example with a Trost or jet mill. Milled iron typically has a 10 to 400 micron particle size, and micronized iron typically has a 0.5 to 10 micron particle size. The required quantity of water is heated to around 65 to 70 degrees Celsius, and the sugar is added, and mixed well until the sugar is dissolved. The solution is cooled to about 30 to 40 degrees Celsius. Povidone, for example, is added and mixed vigorously until dissolved. Iron is added to the mixture and mixed well to uniformly disperse the iron, microcrystalline cellulose is added, and the mixture stirred to provide a uniform suspension. Additional water is added if necessary and the suspension is continuously mixed during the coating process.

Further details of the iron sugar overcoating process are now provided. Briefly, a panning technique can be employed for the tablet coating process. This process can be manual or automated. A traditional sugar-coating pan, or a rotatable circular metal pan mounted angularly on a stand, can be used along with a ladle to apply the coating syrup to the tablets. After coating syrup is applied, a supply of drying air (preferably of variable temperature and thermostatically controlled) and a fan to assist in the removal of dust- and moisture-laden air, are utilized. Sugar coating is generally an aqueous process in which the tablet cores are thoroughly wetted by syrup applications. Therefore, it is usually desirable to utilize a tablet sealant first, for example a shellac, to protect the tablet cores from the action of water and water-soluble polymers, such as Povidone, when applying the sugar syrup. This prevents core disintegration from occurring during the overcoating process.

When the tablet core of the solid oral formulation is relatively large, the iron sugar overcoat can be made thinner, with as little as one coating application, although this may be less desirable. When the tablet core is a small pellet or granule, the iron sugar overcoat can be made much thicker, such as with several coating and drying applications. The tablet should ideally have a completely smooth surface with no visible edges remaining from the original tablet core. Subcoating round surface edges and to build up tablet size to the desired profile may therefore be employed with sugar syrup preferably containing iron before the final iron sugar overcoat is applied. Excipients, such as bulking agents like microcrystalline cellulose or gums can be added to the subcoating suspension. It was found that dosage uniformity of the iron in the iron sugar overcoat can also be increased by the number of iron-containing sugar coats applied to the tablet core, resulting in better iron distribution.

The solution used in subcoating is preferably a less digestible sugar having a laxative effect, such as polydextrose, and contains Povidone and a bioavailable form of iron. Or, the subcoating solution can also contain gum. Subcoating can be accomplished by two methods. The first method is the application of the subcoating solution followed by dusting with powder, such as bulking agents like microcrystalline cellulose, and then drying. This routine is repeated many times until the desired shape is achieved. The second method is the application of a suspension of dry powder in the gum-containing subcoating solution followed by drying. This procedure is repeatedly performed until the correct shape is achieved. The gum will aid in the adhesion of the powder fillers such as microcrystalline cellulose. If a coating suspension is used then the solids content is made as high as possible in order to reduce the drying time between each application.

It is preferable that the applications of iron sugar syrup also contain coloring excipients, for example, pigments and/or titanium dioxide. In some embodiments, one or more final dilute syrup (e.g., polydextrose plus water solution) applications may be employed as a smoothing step to cover and fill any imperfections in the tablet surface caused by the iron sugar overcoat. The iron sugar overcoat is thus made perfectly smooth by successive applications of dilute syrup. The tablets are subjected to drying air after each application.

After the tablets have been made smooth, an optional polishing step can be used to achieve a glossy appearance. The tablets may receive one or two applications of a wax, such as carnauba wax, dissolved in an organic solvent. The polish coat may be applied as a dispersion in a solvent, such as mineral spirits.

When the iron sugar overcoat suspension is too viscous to be sprayed, a sugar-coating pan is employed and the iron sugar overcoat syrup is poured onto the tablets. In other embodiments, when the iron sugar overcoat solution is not too viscous to be sprayed, the mixture may be spray coated onto a tablet core or pellet/granule in small portions, and air dried in between portions, until the desired iron sugar overcoat thickness is formed. This process can be repeated multiple times.

During the manufacturing process, the majority of the water is removed, such that approximately less than 5% water remains in each tablet. Typically less than 2% residual water is present in each tablet.

In general, the formulations of this invention are most desirably administered at a concentration that will generally afford effective results without causing any harmful or deleterious side effects. The dosage requirements may vary the severity of the symptoms presented and the particular subject being treated. In the above four examples, the elemental iron equivalent content of the iron sugar overcoat ranged from about 2 mg to about 18 mg, however, the iron sugar overcoat could have an elemental iron equivalent content of about 0.01 mg to about 27 mg, or more, e.g., 65 mg. In some alternate embodiments, the tablet core is inert with no active ingredients, or serves as a placebo core. These examples are not meant to be exhaustive nor limiting.

Note that treating iron deficiency anemia with lower doses of daily iron takes considerably longer than with higher doses of daily iron. Because tablets according to the invention can be taken multiple times per day and per administration, the invention provides great ability to customize its iron content and the amount of iron to be consumed each day, and can be commensurate with periodic blood iron diagnostic testing.

A method of administering one or more daily solid oral formulation doses of iron contained in an iron sugar overcoat, along with a tablet core containing iron for treating iron deficiency or anemia; then switching to daily administration of a tablet with a similar iron sugar overcoat, but with an inert or different tablet core not containing iron, such as for iron maintenance, is also unique to the present invention. In other methods, the iron content in both the tablet core and/or the iron sugar overcoat differs between at least two different solid oral formulations according to the present invention and taken successively.

Ideally, an at least two-phase treatment method is disclosed by which iron deficiency/iron deficiency anemia is treated in phase-one with a higher iron dose solid oral formulation according to the invention; while iron levels are maintained with a lower iron dose solid oral formulation according to the present invention to prevent the iron deficiency/iron deficiency anemia from returning in phase-two. A third phase can even be envisioned whereby an even lower iron dose solid oral formulation according to the present invention provides just a recommended daily supply of iron.

The at least two-phase method includes a phase-one step of administering daily, for at least three weeks, an at least one dosage of a first solid oral formulation, said first solid oral formulation includes a tablet core and an iron sugar overcoat that includes at least one form of iron and at least one sugar that has some laxative effect that counteracts at least some of the constipation associated with oral iron consumption, said first solid oral formulation includes iron in a higher initial amount sufficient to be available for gastrointestinal absorption for treating iron deficiency/iron deficiency anemia. The method further includes a phase-two step of reducing the administering daily of the at least one dosage of the first solid oral formulation after the at least three weeks from when dosage administration of said first solid oral formulation began in phase-one. This is done concomitantly while administering daily at least one dosage of a second solid oral formulation in phase-two. The second solid oral formulation of phase-two includes a tablet core and an iron sugar overcoat that includes at least one form of iron and at least one sugar that has some laxative effect that counteracts at least some of the constipation associated with oral iron consumption. The second solid oral formulation includes iron in a lower subsequent amount sufficient to be available for gastrointestinal absorption for replenishing/maintaining iron levels in the body and preventing recurrence of iron deficiency/iron deficiency anemia. In other words, the second solid oral formulation has an elemental iron equivalent content that is less than that of the first solid oral formulation. The amount of iron available for absorption is reduced in each subsequent phase of this method, but can be increased when needed. The method may therefore be adjusted based on the results of blood iron levels derived from periodic diagnostic blood testing.

Other variations and embodiments of the invention described herein will now be apparent to those of skill in the art without departing from the disclosure of the invention or the coverage of the claims to follow.

What is claimed as being new and desired to be protected by Letters Patent of the United States is as follows:

1. A solid oral formulation including a tablet core and an iron sugar overcoat; said tablet core including at least one therapeutic ingredient, said tablet core further surrounded by said iron sugar overcoat; said iron sugar overcoat including at least one form of bioavailable iron and at least one sugar, said at least one form of bioavailable iron and said at least one sugar each in an amount of at least 0.01 mg, said iron sugar overcoat making available at least some elemental iron content for gastrointestinal absorption prior to release of said at least one therapeutic ingredient of said tablet core; said at least one sugar of said iron sugar overcoat further having some laxative effect that counteracts at least some constipation associated with oral iron consumption.

2. The at least one form of bioavailable iron of said iron sugar overcoat according to claim 1 further priming iron transporters in intestines prior to absorption of said at least one therapeutic ingredient of said tablet core.

3. The at least one form of bioavailable iron of said iron sugar overcoat according to claim 1 further having at least one physical effect selected from the group consisting of reducing gastrointestinal bleeding, maintaining iron levels, replenishing iron levels, raising iron levels, preventing iron deficiency anemia, preventing iron deficiency, treating iron deficiency, and treating iron deficiency anemia.

4. The at least one form of bioavailable iron of said iron sugar overcoat according to claim 1 is selected from the group consisting of compounds and molecules containing ferrous iron, compounds and molecules containing ferric iron, iron salts, ferric sulfate, ferrous sulfate, ferrous fumarate, ferrous gluconate, sodium ferric gluconate, iron amino chelate, iron polymaltose complex, carbonyl iron, and heme derived iron.

5. The iron sugar overcoat according to claim 1 further having some sweet taste to mask the taste of said at least one form of bioavailable iron in said iron sugar overcoat.

6. The at least one sugar of said iron sugar overcoat according to claim 1 further selected from the class of sugars behaving as soluble fiber.

7. The at least one sugar of said iron sugar overcoat according to claim 1 further selected from the class of sugar alcohols.

8. The at least one sugar of said iron sugar overcoat according to claim 1 further selected from the class of less digestible/hard-to-digest sugars.

9. The iron sugar overcoat according to claim 1 further including at least one excipient.

10. The iron sugar overcoat according to claim 1 further including at least one excipient selected from surface modifying agents, solvents, and binders.

11. The iron sugar overcoat according to claim 1 further including at least one additional ingredient, and at least one pharmaceutically active ingredient other than a form of bioavailable iron and sugar laxative.

12. The tablet core according to claim 1 structured as a pellet/granule.

13. The tablet core according to claim 1 further including at least one excipient.

14. The tablet core according to claim 1 further including at least one excipient selected from fillers, binders, solvents, coating excipients, and release-modifying excipients.

15. The at least one therapeutic ingredient of said tablet core according to claim 1 is selected from the group consisting of vitamins, minerals, proteins, carbohydrates, and lipids.

16. The at least one therapeutic ingredient of said tablet core according to claim 1 is a bioavailable form of iron selected from the group consisting of compounds and molecules containing ferrous iron, compounds and molecules containing ferric iron, iron salts, ferric sulfate, ferrous sulfate, ferrous fumarate, ferrous gluconate, sodium ferric gluconate, iron amino chelate, iron polymaltose complex, carbonyl iron, and heme derived iron.

17. The at least one therapeutic ingredient of said tablet core according to claim 1 is a bioavailable form of iron in an amount of at least 0.1 mg and further having at least one physical effect selected from the group consisting of reducing gastrointestinal bleeding, maintaining iron levels, replenishing iron levels, raising iron levels, preventing iron deficiency anemia, preventing iron deficiency, treating iron deficiency, and treating iron deficiency anemia.

18. The at least one therapeutic ingredient of said tablet core according to claim 1 is an active pharmaceutical ingredient and not a dietary supplement ingredient.

19. The at least one therapeutic ingredient of said tablet core according to claim 1 is a nonsteroidal anti-inflammatory drug.

20. The at least one therapeutic ingredient of said tablet core according to claim 1 is selected from anticholinergics.

21. A solid oral formulation including a tablet core and an iron sugar overcoat; said tablet core including at least one therapeutic ingredient, said tablet core further surrounded by said iron sugar overcoat; said iron sugar overcoat including at least one form of bioavailable iron and at least one sugar, said at least one form of bioavailable iron and said at least one sugar each in an amount of at least 0.01 mg, said iron sugar overcoat making available at least some elemental iron content for gastrointestinal co-absorption with said at least one therapeutic ingredient of said tablet core.

22. An at least two-phase method including a phase-one step of administering daily, for at least three weeks, an at least one dosage of a first solid oral formulation, said first solid oral formulation including a tablet core and an iron sugar overcoat including at least one form of iron in an amount of at least 0.01 mg and at least one sugar in an amount of at least 0.01 mg having some laxative effect that counteracts at least some constipation associated with oral iron consumption, said first solid oral formulation including iron in a higher initial amount sufficient to be available for gastrointestinal absorption for treating iron deficiency/iron deficiency anemia;

said method further including a phase-two step of reducing said administering daily of said at least one dosage of said first solid oral formulation after the at least three weeks from when dosage administration of said first solid oral formulation began in phase-one; while concomitantly administering daily at least one dosage of a second solid oral formulation, said second solid oral formulation including a tablet core and an iron sugar overcoat including at least one form of iron in an amount of at least 0.01 mg and at least one sugar in an amount of at least 0.01 mg having some laxative effect that counteracts at least some constipation associated with oral iron consumption, said second solid oral formulation including iron in a lower subsequent amount sufficient to be available for gastrointestinal absorption for replenishing/maintaining iron levels and preventing recurrence of iron deficiency/iron deficiency anemia; said second solid oral formulation having an elemental iron equivalent content less than that of said first solid oral formulation.

\* \* \* \* \*